US008771706B2

(12) United States Patent
Anderson et al.

(10) Patent No.: US 8,771,706 B2
(45) Date of Patent: Jul. 8, 2014

(54) ANTI-RSV IMMUNOGENS AND METHODS OF IMMUNIZATION

(71) Applicant: The United States of America being represented by the Secretary of the Department of, Washington, DC (US)

(72) Inventors: Larry J. Anderson, Atlanta, GA (US); Lia M. Haynes, Lithonia, GA (US); Ralph A. Tripp, Decatur, GA (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/763,822

(22) Filed: Feb. 11, 2013

(65) Prior Publication Data
US 2013/0136759 A1 May 30, 2013

Related U.S. Application Data

(62) Division of application No. 13/388,839, filed as application No. PCT/US2010/044434 on Aug. 4, 2010.

(60) Provisional application No. 61/231,162, filed on Aug. 4, 2009, provisional application No. 61/333,496, filed on May 11, 2010.

(51) Int. Cl.
*A61K 39/155* (2006.01)
(52) U.S. Cl.
USPC ..................................... 424/211.1; 424/186.1
(58) Field of Classification Search
CPC ... A61K 39/155; A61K 38/162; C07K 14/005
See application file for complete search history.

(56) References Cited

U.S. PATENT DOCUMENTS

| 6,077,511 | A | 6/2000 | Langedijk | |
|---|---|---|---|---|
| 6,113,911 | A | 9/2000 | Binz et al. | |
| 2003/0064078 | A1 | 4/2003 | Binz et al. | |
| 2005/0042230 | A1* | 2/2005 | Anderson et al. | 424/186.1 |
| 2009/0181042 | A1 | 7/2009 | Corvaia et al. | |
| 2010/0203071 | A1* | 8/2010 | Blais et al. | 424/186.1 |

FOREIGN PATENT DOCUMENTS

| AU | 756110 B2 | 1/2003 |
|---|---|---|
| CA | 2257943 A1 | 12/1997 |
| CA | 2302833 A1 | 3/1999 |
| WO | WO-97-46581 A1 | 12/1997 |
| WO | WO9903987 | 1/1999 |
| WO | WO-9914334 A1 | 3/1999 |

OTHER PUBLICATIONS

GenBank: M55633.1, published on Aug. 3, 1993. http://www.ncbi.nlm.nih.gov/nuccore/M55633.1.*
Johnson TR et al. Respiratory syncytial virus (RSV) G glycoprotein is not necessary for vaccine-enhanced disease induced by immunization with formalin-inactivated RSV. J Virol. Jun. 2004;78(11):6024-32.*
Imai, et al.; Identification and Molecular Characterization of Fractalkine Receptor CX3CR1, which Mediates Both Leukodyte Migration and Adhesion, (1997) Cell, vol. 91: 521-530.
Mizoue, et al.; Solution Structure and Dynamics of the CX3C Chemokine Domain of Fractalkine and its Interaction with an N-terminal Fragment of CX3CR1; (1999) Biochemistry 38; 1402-1414.
Cane, et al.; Identification of variable domains of the attachment (G) protein of subgroup A respiratory syncytial viruses; (1991) Journal of General Virology 72:2091-2096.
Tripp, et al.; CX3C Chemokine Mimicry by respiratory syncytial virus G glycoprotein, (2001) Nature Immunology 2(8): 732-738.
Levine, et al., Demonstration that Glycoprotein G is the Attachment Protein of Respiratory Syncytial Virus; (1987) J. Gen. Virol. 68:2521-2524.
Walsh, et al.; Comparison of Antigenic Sites of Subtype-specific Respiratory Syncytial Virus Attachment Proteins, (1989) J. Gen. Virol. 70:2953-2961.
Simard et al.; Subgroup specific protection of mice from respiratory syncytial virus infection with peptides encompassing the amino acid region 174-187 from the G glycoprotein: the role of cysteinyl residues in protection; (1997) Vaccine 15:423-432.
Trudel, et al.; Protection of BALBC/C Mice from Respiratory Syncytial Virus Infection by Immunization with a Synthetic Peptide Derived from the G Glycoprotein, (1991) Virology 185: 749-757.
Norrby; et al.; Site Directed serology with synthetic peptides representing the large glycoprotein G of respiratory syncytial virus (1987) PNAS(USA) 84: 6572-6576.
Anderson, et al.; Indentification of Epitopes on Respiratory Syncytial Virus Proteins by Competitive Binding Immunoassay; (1986) Journal of Clinical Microbiology 23(3): 475-480.
Akerlind-Stopner, et al.; A Subgroup Specific Antigenic Site in the G Protein of Respiratory Syncytial Virus Forms a Disulfide-Bonded Loop; (1990) J. Virol. 64(10): 5143-5148.
Plotnicky-Gilquin, et al.; Indentification of Multiple Protective Epitopes (Protectopes) in the Central Conserved Domain of a Prototype Human Respiratory Syncytial Virus G Protein; (1999) J. Virol. 73(7): 5637-5645.
Domachowske and Rosenberg; Respiratory Syncytial Virus Infection: Immune Response, Immunopathogenesis and Treatment; (1999) Clinical Microbiology Reviews 12(2): 298-309.

(Continued)

*Primary Examiner* — Mary E Mosher
*Assistant Examiner* — Nick Zou
(74) *Attorney, Agent, or Firm* — Gifford, Krass, Sprinkle, Anderson & Citkowski, P.C.

(57) ABSTRACT

Immunogenic polypeptides corresponding to one or more RSV G glycoproteins, or analogs thereof, are provided as components of vaccines. The inventive compositions are useful as both a prophylactic and therapeutic for the prevention and treatment of RSV infections and associated pulmonary or other diseases. The inventive immunogens include regions of the RSV G protein, specifically, amino acid residues 164-176 of RSV G A2 protein or analogs thereof. This inventive immunogen is operable alone or in combination with other polypeptides such as the RSV G protein amino acid residues 155-206, or other vaccines such as live RSV vaccines, or inactivated RSV vaccines or immunogenic analogs thereof.

10 Claims, 5 Drawing Sheets

(56) References Cited

OTHER PUBLICATIONS

Weltzin, R.; The therapeutic potential of monoclonal antibodies against respiratory syncytial virus; (1998) Expert Opinion on Investigational Drugs 7(8): 1271-1283.
Zambon, M.; Active and Passive Immunisation against Respiratory Syncytial Virus: Rev. Med. Virol. 9: 227-236 (1999).
Martinez and Melero; Enhanced neutralization of human respiratory syncytial virus by mixtures of monoclonal antibodies to the attachment (G) glycoprotein; (1998) J. Gen. Virol. 79: 2215-2220.
Feng et al.; Kidney International 1999 vol. 56, pp. 612-620.
Anderson et al.; Antigenic characterization of respiratory syncytial virus strains with monoclonal antibodies. J. Infect. Dis. 15:626-633 (1985).
Beisser et al.; Human cytomegalovirus chemokine receptor gene US28 is transcribed in latently infected THP-1 monocytes. J. Virol. 75:5949-5957 (2001).
Bourgeois et al.; Heparin-like structures on respiratory syncytial virus are involved in its infectivity in vitro. J. Virol. 72(9): 7221-7227 (1998).
Boyden; The chemotactic effect of mixtures of antibody and antigen on polymorphonuclear leukocytes. J. Exp. Med. 115:453-466 (1962).
Brake et al.; Alpha-factor directed synthesis and secretion of mature foreign proteins in *Saccharomyces cerevisiae*. PNAS 82:4642-4646 (1984).
Bright et al.; Comparison of the T helper cell response induced by respiratory syncytial virus and its fusion protein in BALB/c mice. Vaccine 13:915-922 (1995).
Chanock et al.; Serious respiratory tract disease caused by respiratory syncytial virus; prospects for improved therapy and effective immunization, Pediatrics 90:137-143 (1992).
Chin et al.; Field evaluation of a respiratory syncytial virus vaccine and a trivalent parainfluenza virus vaccine in a pediatric population; Am. J. Epidemiol. 89(4): 449-463 (1969).
Combadiere et al.; Gene cloning, RNA distribution, and functional expression of mCX3CR1, a mouse chemotactic receptor for the CX3C chemokine fractalkine. Bio. & Biopys. Res. Comm. 253:728-732 (1998).
Combadiere et al.; Identification of CX3CR1. A chemotactic receptor for the human CX3C chemokine fractalkine and a fusion coreceptor for HIV-1. J. Biol. Chem. 273:23799-23804 (1998).
Connors et al.; Respiratory syncytial virus (RSV) F, G, M2 (22K), and N proteins each induce resistance to RSV challenge, but resistance to RSV challenge, but resistance induced by M2 and N proteins is relatively short-lived. J. Virol. 65:1634-1637 (1991).
Crowe et al.; Recombinant human respiratory syncytial virus (RSV) monoclonal antibody Fab is effective therapeutically when introduced directly into the lungs of RSV-infected mice. Proc Natl. Acad. Sci. USA 91: 1386-90 (1994).
Driscoll. Macrophage inflammatory proteins: biology and role in pulmonary inflammation. Exp. Lung Res. 20:473-490 (1994).
Endres et al.; The Kaposi's sarcoma-related herpes virus (KHSV)-encoded chemokine vMIP-1 is a specific agonist for the CC chemokine receptor (CCR)8. J. Exp. Med. 189: 1993-1998 (1999).
Feldman et al.; Identification of a linear heparin binding domain for human respiratory syncytial virus attachment glycoprotein G. J. Virol. 73:6610-6617 (1999).
Feldman et al.; The fusion glycoprotein of human respiratory syncytial virus facilitates virus attachment and infectivity via an interaction with cellular heparin sulfate. J. Virol. 74:6442-6447 (2000).
Fixler. Respiratory syncytial virus infection in children with congenital heart disease: a review. Ped. Cardiol. 17:163-168 (1996).
Fong et al.; Fractalkine and CX3CR1 mediate a novel mechanism of leukocyte capture, firm adhesion, and activation under physiologic flow. J. Exp. Med. 188:1413-1419 (1998).
Graham et al.; Priming immunization determines T helper cytokine mRNA expression patterns in lungs of mice challenged with respiratory syncytial virus J. Immunol. 151:2032-2040 (1993).
Groothuis et al.; Safety and immunogenicity of a purified F protein respiratory syncytial virus (PFP-2) vaccine in seropositive children with bronchopulmonary dysplasia. J. Infect. Dis. 177:467-469 (1998).
Hall; Respiratory syncytial virus: a continuing culprit and conundrum. J. Ped. 135:2-7 (1999).
Hallak et al.; Iduronic acid-containing glycosaminoglycans on target cells are required for efficient respiratory syncytial virus infection. Virol. 271:264-275 (2000).
Hancock et al.; Generation of atypical pulmonary inflammatory responses in BALB/c mice after immunization with the native attachment (G) glycoprotein of respiratory syncytial virus. J. Virol. 70:7783-7791 (1996).
Johnson et al.; Priming with secreted glycoprotein G of respiratory syncytial virus (RSV) augments interleukin-5 production and tissue eosinophilia after RSV challenge. J. Virol. 72:2871-2880 (1998).
Johnson et al.; The G glycoprotein of human respiratory syncytial viruses of subgroups A and B: extensive sequence divergence between antigenically related proteins. Proc. Nat. Acad. Sci. USA 84:5625-5629 (1987).
Jones et al.; Replacing the complementarily-determining regions in a human antibody with those from a mouse. Nature 321:522-525 (1986).
Karron et al.; Respiratory syncytial virus (RSV) SH and RSV G glycoproteins are not essential for viral replication in vitro: clinical evaluation and molecular characterization of a cold-passaged, attenuated RSV subgroup B mutant. Proc. Nat. Acad. Sci. USA 94:13961-13966 (1997).
Kearney et al.; a New Mouse Myeoma Cell Line that has Lost Immunoglobulin Expression but Permits the Construction of Antibody-Secreting Hybrid Cell Lines. J. Immunol. 123(4):1548-1550 (1979).
Koopmann et al.; Structure and function of the glycosaminoglycan binding site of chemokine macrophage-inflammatory protein-1 beta. J. Immunol. 163:2120-2127 (1999).
Kurt-Jones et al.; Pattern recognition receptors TLR4 and CD14 mediate response to respiratory syncytial virus. Nature Immunol. 1:398-401 (2000).
Lalani et al.; The purified myxoma virus gamma interferon receptor homolog M-T7 interacts with heparin-binding domains of chemokines. J. Virol.71:4356-4363 (1997).
Loetscher et al.; Chemokines and their receptors in lymphocyte trafficking and HIV infection. Adv. Immunol. 74:127-180 (2000).
Martinez et al.; Antigenic structure of the human respiratory syncytial virus G glycoprotein and relevance of hypermutation events for the generation of antigenic variants. J. Gen. Virol. 78:2419-2429 (1997).
McDermott et al.; Chemokines and their receptors in infectious disease. Springer Sem. Immunopathol. 22:393-415 (2000).
McIntosh et al.; Immunopathologic mechanisms in lower respiratory tract disease of infants due to respiratory syncytia virus. Prog. Med. Viro. 26:94-118 (1980).
Melero et al.; Antigenic structure, evolution and immunobiology of human respiratory syncytial virus attachment (G) protein. J. Gen. Virol. 75:2411-2418 (1997).
Michieli et al.; Inhibition of oncogene-mediated transformation by ectopic expression of p21 Waf1 in NIH3T3 cells. Oncogene 12:775-784 (1996).
Olmsted et al.; Expression of the F glycoprotein of respiratory syncutial virus by a recombinant vaccinia virus: comparison of the individual contributions of the F and G glycoproteins to host immunity. Proc. Nat. Acad. Sci. USA 83:7462-7466 (1986).
Openshaw. Immunity and Immunopathology to respiratory syncytial virus. The mouse model. Amer. J. Respir. & Crit. Care Med. 152:859-862 (1995).
Pelchen-Matthews et al.; Chemokine receptor trafficking and viral replication. Immunol. Rev. 168:33-49 (1999).
Roder et al.; Purification of respiratory syncytial virus F and RSV G glycoproteins. J. Chromat. 737:97-106 (2000).
Schall. Fractalkine—a strange attractor in the chemokine landscape. Immunol. Today 18:147-152 (1997).

(56) References Cited

OTHER PUBLICATIONS

Sparer et al.; Eliminating a region of respiratory syncytial virus attachment protein allows induction of protective immunity without vaccine-enhanced lung eosinophilia.; J. Exp. Med. 187: 1921-1926 (1998).
Srikiatkhachorn et al.; Virus-specific memory and effector T lymphocytes exhibit different cytokine responses to antigens during experimental murine respiratory syncytial virus infection. J. Virol. 71:678-685 (1997).
Stott et al.; Immune and histopathological responses in animals vaccinated with recombinant vaccine viruses that express individual genes of human respiratory syncytial virus. J. Virol. 61:3855-3861 (1987).
Sullender. Antigenic analysis of chimeric and truncated RSV G glycoproteins of respiratory syncytial virus. Virol. 209:70-79 (1995).
Tebbey et al.; Atypical pulmonary eosinophilia is mediated by a specific amino acid sequence of the attachment (G) protein of respiratory syncytial virus. J. Exp. Med. 188: 1967-1972 (1998).
Tempest et al.; Reshaping a Human Monoclonal antibody to Inhibit Human Respiratory Syncytial Virus Infection in Vivo. Biotechnology 9:266-271 (1991).
Tripp et al; Cytotoxic T-lymphocyte precursor frequencies in BALB/c mice after acute respiratory syncytial virus (RSV) infection or immunization with a formalin-inactivated RSV vaccine. J. Virol. 72:8971-8975 (1998).
Tripp et al.; Respiratory syncytial virus (RSV) G and/or SH proteins alter Th1 cytokines, natural killer cells and neutrophils responding to pulmonary infection in BALB/c mice. J. Virol. 73:7099-7107 (1999).
Tripp et al.; Respiratory syncytial virus G and/or SH glycoproteins modify CC and CXC chemokine mRNA expression in the BALB/c mouse. J. Virol. 74:6227-6229 (2000).
Tripp et al.; TH(1)- and TH(2)- TYPE cytokine expression by activated t lymphocytes from the lung and spleen during the inflammatory response to respiratory syncytial virus. Cytokine 12:801-807 (2000).
Tripp et al.; Respiratory syncytial virus infection and G and/or SH protein expression contribute to substance P, which mediates inflammation and enhanced pulmonary disease in BALB/c mice. J. Virol. 74:1614-1622 (2000).
Tripp et al.; CX3C chemokine mimicry by respiratory syncytial virus G glycoprotein. Nature Immunology 2(8): 732-738 Abstract (2001).
Weibel et al.; Respiratory virus vaccines. V. field evaluation for efficacy of heptavalent vaccine. Am. Rev. Resp. Dis. 94:362-379 (1996).
Witt et al.; Differential binding of chemokines to glycosaminoglycan subpopulations. Curr. Biol. 4:394-400 (1994).
Zhang et al.; Expression of respiratory syncytial virus-induced chemokine gene networks in lower airway epithelial cells revealed by cDNA microarrays. J. Virol. 75(19):9044-9058 (2001).
Corbeil, et al.; Involvement of the complement system in the protection of mice from challenge with respiratory syncytial virus Long strain following passive immunization with monoclonal antibody 18A2B2, Vaccine, vol. 14, Issue 6, Apr. 1996, pp. 521-525.
Wathen MW; J Gen Virol. Oct. 1989; 70 (Pt 10):2625-35.; Related Articles, Links Characterization of a novel human respiratory syncytial virus chimeric FG glycoprotein expressed using a baculovirus vector.
Wathen et al.; J Infect Dis. Mar. 1991; 163(3):477-82. Vaccination of cotton rats with a chimeric FG glycoprotein of human respiratory syncytial virus induces minimal pulmonary pathology on challenge.
Murphy et al.; Virus Research 1994 vol. 32 pp. 13-36.

\* cited by examiner

Solid squares represent control antibody treated mice. Open triangles represent anti-RSV G antibody treated (low-dose) mice. The open squares represent anti-RSV G antibody treated (high-dose) treated mice.

US 8,771,706 B2

ANTI-RSV IMMUNOGENS AND METHODS OF IMMUNIZATION

CROSS REFERENCE TO RELATED APPLICATIONS

This application is a divisional of U.S. application Ser. No. 13/388,839, which is the U.S. National Stage of PCT/US2010/044434, filed Aug. 4, 2010, and which claims priority to U.S. Provisional Application No. 61/231,162 filed Aug. 4, 2009 and U.S. Provisional Application No. 61/333,496 filed May 11, 2010, the entire contents of each of which are incorporated herein by reference.

FIELD OF THE INVENTION

The invention relates generally to poly-amino acid immunogens. More specifically, the invention relates to polypeptides related to RSV-G glycoprotein that induces an immune response in a subject. The peptides promote immunity to RSV infection while preventing undesirable immunological responses in a subject.

BACKGROUND OF THE INVENTION

Respiratory syncytial virus (RSV) is the most common cause of serious lower respiratory illness in infants and young children worldwide. Immunoprotection is incomplete after a subject has been exposed to RSV such that repeat infections occur throughout life often with serious complications in the elderly and immune compromised patients. Unfortunately, while numerous vaccine candidates have been proposed and studied, there is no safe and effective vaccine available and treatment options are limited.

RSV displays two major surface viral proteins, the G (attachment) and the F (fusion) glycoproteins. The RSV F glycoprotein is much more effective in inducing protective immunity in animal model systems. Consequently, efforts to treat and prevent RSV infection have often focused on anti-RSV F protein antibodies, antiviral drugs that affect the F protein, and live virus or F protein-based vaccines. For example, prophylactic treatment with a palivizumab (a neutralizing, anti-RSV F protein monoclonal antibody) decreases the incidence of serious RSV induced infection in high-risk infants and young children. Palivizumab is not effective in treating active infection and as such is limited in its use. Similarly, other treatments for acute RSV infection also proved ineffective or minimally effective. For example, the antiviral Ribavirin has limited efficacy and is seldom used except for treatment of infection in immunocompromised patients. Without being limited to a single hypothesis, one possible explanation for the ineffectiveness of existing RSV treatments is that the virus-induced host inflammatory response is important to disease pathogenesis and this inflammatory response is only partially responsive to antiviral therapy once infection is established. Consequently, effective treatment may require both anti-inflammatory and antiviral components.

The G protein of RSV may play a role in inducing and modulating the host immune response to infection. Intact RSV G protein expression in the infecting virus is associated with a lower frequency of IFNγ expressing cells and a higher frequency of IL-4 expressing cells. RSV G protein has also been associated with increased pulmonary eosinophilia after RSV challenge in formalin-inactivated RSV vaccinated mice, increased pulmonary levels of substance P in RSV challenged mice, and decreased respiratory rates associated with its administration to mice.

Efforts to make a safe and effective vaccine have failed to date. One problem in developing a vaccine is the fact that a formalin inactivated vaccine led to more serious disease with later RSV infection when administered to young children, leading to concerns that any non-live RSV vaccine may be unsafe in young children. Another problem with prior art vaccines is an inability to induce a highly effective protective immune response. This problem is highlighted by the fact that natural infection provides only limited protection from reinfection and disease.

As such, there is a need for a safe and effective vaccine for RSV.

SUMMARY OF THE INVENTION

The present invention provides a single or multi-component vaccine that has one or more isolated immunogens related to the RSV G protein. Inventive vaccines include one or more immunogens corresponding to fragments of RSV G protein including residues 164-176, residues 163-190, and residues 155-206 of SEQ ID NOs 1, 7, 8, or analogues thereof. Optionally, the immunogens are amino acid sequences corresponding to one or more of SEQ ID NOs: 2-6, or analogues thereof. The immunogens produce antibodies or otherwise produce an immune response in an immunized subject. One or more immunogens optionally include a tag to assist in isolation of the immunogen. An immunogen is optionally recombinant.

In a multi-component vaccine (i.e. at least a first and a second immunogen) the immunogens are optionally associated by a linker. Association is optionally covalent. A linker is optionally an intermediate polypeptide fragment that may be excisable. In some embodiments the immunogens of a multi-component vaccine are the polypeptides of SEQ ID NOs: 3, 4, 5, 6, or analogues thereof.

Inventive vaccines optionally contain an adjuvant illustratively dimethyl dioctadecyl-ammonium bromide (DDA); monophosphoryl lipid A (MPL); LTK63, lipophilic quaternary ammonium salt-DDA, DDA-MPL, aluminum salts, aluminum hydroxide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04, ZADAXIN, or combinations thereof.

The inventive vaccines optionally contain an emulsification agent illustratively supramolecular biovectors (SMBV), nanoparticles, liposomes, or combinations thereof.

The invention also provides a process of creating an immune response in a subject. Optionally, the process includes administering an inventive immunogen or polypeptide to a subject. Administration is by any effective method known in the art illustratively subcutaneous, intramuscular, intranasal, oral, intravaginal, intravenous, intramucosal, or combinations thereof.

More than one vaccine is optionally administered to a subject. A second vaccine is optionally administered prior to, simultaneously with, or subsequent to administration of a first vaccine. It is appreciated that a second vaccine is optionally an amino acid sequence corresponding to amino acid position 155 to amino acid position 206 of SEQ ID NO: 1 or an analogue thereof; or an amino acid sequence corresponding to amino acid position 163 to amino acid position 190 of SEQ ID NOs: 1, 7, 8, or an analogue thereof; or a combination thereof.

Optionally, the present invention is administered to make another RSV vaccine safer by inducing antibodies that protect from an aberrant or enhanced response to otherwise induced by the different type of RSV vaccine.

Also provided is a pharmaceutical package including a vaccine with one or more immunogens of the subject invention, an emulsification agent and an adjuvant.

DETAILED DESCRIPTION OF THE PREFERRED EMBODIMENTS

Figure 1A:
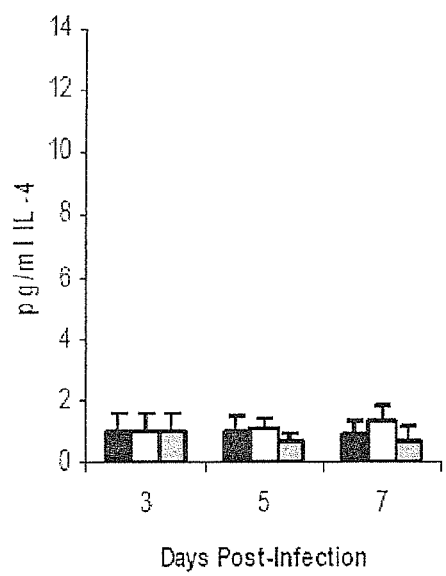
FIG. 1 represents the relative levels of IL-4 (A) or IFNγ (B) in mice challenged with RSV that were either treated or not treated with antibodies that bind the G protein similar to those induced by the inventive immunogens where the black bars represent control antibody treated mice, the open bars represent anti-RSV G antibody treated (low-dose or 150 µg) mice, and the gray bars represent anti-RSV G antibody treated (high-dose or 300 µg) treated mice.

The present invention may be understood more readily by reference to the following detailed description of the preferred embodiments of the invention and the Examples included herein.

Before the present compounds and methods are disclosed and described, it is to be understood that this invention is not limited to specific proteins, specific methods, or specific nucleic acids, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise.

The present invention both results in an effective and protective immune response, but also does not suffer the propensity to induce more serious disease similar to the formalin inactivated respiratory syncytial virus (RSV) vaccines of the prior art. As such, the present invention has utility as an immunogen and method of immunization against infection by RSV.

An aspect of this invention provides non-live RSV vaccines which are produced, or non-live RSV vaccines which are improved, by selecting regions of the RSV G glycoprotein so that when the vaccines are administered to a human or animal higher titers of antibodies are produced that block the biological action of polypeptide portions of the G glycoproteins of subsequently-infecting RSV viruses or promote removal of viruses or infected cells.

In another aspect of this invention vaccines are provided which when administered to a human or animal, induce an immune response such as the production of antibodies that block or otherwise alter the biological function of the G glycoprotein of subsequently-infecting RSV viruses. Alternatively, the vaccine includes one or more G glycoprotein peptides or polypeptides, or analogues thereof, from different RSV strains having the foregoing ability. RSV strains illustratively include those expressing RSVGA, RSVGA2, RSVGA_CH17 or RSVB G glycoprotein.

Also provided is a method for improving or identifying drugs, antibodies, peptides, polypeptides or other blocking molecules that can be used to treat RSV disease and/or to be used as vaccines to prevent RSV disease.

The present invention employs a polypeptide that includes a 13 amino acid sequence of the RSV G protein (aa 164 to 176 in the A2 strain of RSV) or an immunogenic analogue thereof, the RSV G protein (RSVGA_CH17 synthetic aa 163-190), the RSVB G protein sequence RSVGB (synthetic aa 155-206) or two polypeptides one each for the RSV group A and B strain specific and conserved regions (illustratively amino acids 163 to 190 for group A and amino acids 155 to 206 for group B strains of RSV) that effectively induce immunoprotective antibodies in a subject. In addition, the 13 aa region is substantially conserved among RSV strains and the combination of the group A and B specific regions are present on all strains such that the inventive vaccines provide broad-based protection.

An immunogen illustratively includes amino acid residues corresponding to amino acids 164 to 176 of SEQ ID NO: 1, or an analogue thereof. Optionally, the immunogen is the amino acid sequence of SEQ ID NO: 2.

In some embodiments an analogue of an immunogen is used as an immunogen. An analog is optionally an immunogen with one or more mutations such as amino acid substitutions, insertions, alterations, modifications, or other amino acid changes that increase, decrease, or not alter the ability of the protein to elicit an immune response in a subject, bind to CX3CR1, or both relative to a wild-type protein. It is appreciated that the CX3C motif is immune modulatory. Altering the amino acid of the motif, or alterations in regions near the motif in a wild type immunogen improves safety while still producing antibodies that block the binding of an immunogen to the receptor CX3CR1. Therefore, it is also appreciated that amino acid insertions, illustratively to produce a CX1C, CX2C, CX4C, CX5C, CX6C to CX10C inclusive, are performed. Optionally, one or more of the cysteine residues in the chemokine motif, CX3C, is altered such as by deletion, substitution, or other modification to the cysteine residue(s) itself. It is appreciated that any combination of the alterations to a wild-type immunogen sequence is envisioned.

Several post-translational modifications are similarly envisioned as within the scope of the present inventions illustratively including incorporation of a non-naturally occurring amino acid(s), phosphorylation, glycosylation, addition of pendent groups such as biotinylation, fluorophores, lumiphores, radioactive groups, antigens, or other molecules all of which are encompassed by the term analogue. An analogue of an immunogen is optionally a fragment of an immunogen. An analogue of an immunogen is a polypeptide that has some level of activity of inducing an immune response in a subject toward a region of the RSV G glycoprotein. An analogue optionally has between 0.1% and 200% the activity of a wild-type immunogen. An analogue of an immunogen is optionally a wild-type RSV G glycoprotein sequence that is altered in at least property relative to the wild-type protein sequence. Such properties illustratively include immunogenicity, thermal stability, pH/stability profile, stability towards oxidation, solubility, or combinations thereof. Methods of synthesizing an immunogen, modifying an immunogen, testing for immunogenic activity or a property of an immunogen analogue illustratively receptor binding, or expressing an immunogen or analogue thereof are achievable by methods ordinarily practiced in the art illustratively by methods disclosed in Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002, the contents of each of which are incorporated herein by reference.

An immunogen illustratively includes amino acid residues corresponding to amino acids 163 to 190 of SEQ ID NOs: 1, 8, or analogues thereof. Optionally, the immunogen is the amino acid sequence of SEQ ID NOs: 4 or 5.

An immunogen illustratively includes amino acid residues corresponding to amino acids 155 to 206 of SEQ ID NO: 7 or an analogue thereof. Optionally, the immunogen is the amino acid sequence of SEQ ID NO: 6.

The term "polypeptide" or "protein" are used interchangeably herein and are illustratively a chain of two or more amino acid residues. An immunogen is illustratively a polypeptide that has some level of immunogenic activity, i.e. the ability to induce the production of antibodies in an organism. In some embodiments, a polypeptide is the amino acid sequence for RSV G protein or analogues thereof used alone or combined with other peptide or otherwise immunogenic sequence(s) or therapeutics. Illustrative examples of RSV G protein sequences are found at GenBank accession number P03423 and SEQ ID NO. 1, as well as accession number P20896 and SEQ ID NO: 7 and SEQ ID NO: 8.

Immunogens are optionally recombinant and obtained by methods known in the art. Illustratively, a nucleotide sequence is cloned into a plasmid which is transfected into *E. coli* and expressed. To ease purification procedures the expressed polypeptides optionally include a tag. Illustrative examples of include poly-histidine, CBP, CYD (covalent yet dissociable NorpD peptide), strep-2, FLAG, HPC or heavy chain of protein C peptide tag, or GST and MBP protein fusion tag systems. It is appreciated that other tag systems are similarly operable. In some embodiments recombinant polypeptides are expressed in *E. coli* and purified using an affinity tag system followed by enzymatic cleavage of the tag such as by incorporating a factor Xa, thrombin, or other enzyme cleavage site in the expressed polypeptide. Methods of tag cleavage are known in the art and any effective method is appreciated to be suitable for use in the instant invention.

An isolated RSV G protein immunogen or analogue thereof is provided. Optionally, an inventive RSV G protein has the sequence represented by SEQ ID NOs: 1, 8, or analogues thereof illustratively, SEQ ID NOs: 2, 3, or 4, or analogues thereof. Optionally, RSV G protein fragment is the sequence represented by SEQ ID NOs: 5 or 6 or analogues thereof. Optionally, RSV G protein has the sequence represented by SEQ ID NO: 7 or an analogue thereof.

RSV G protein is optionally recombinant. However, it is also envisioned that naturally occurring RSV G protein may be isolated from at least a portion of the sample material for which the wild type sequence is normally found. Methods for purification of protein from organism derived samples are known and are within the level of skill in the art.

It is recognized that numerous variants, analogues, or homologues are within the scope of the present invention including amino acid substitutions, alterations, modifications, or other amino acid changes that increase, decrease, or do not alter the function or immunogenic propensity of the inventive immunogen or vaccine. It is further appreciated that the inventive sequences of SEQ ID NOs: 1-8 are optionally modified by the addition of one or more amino acids, sugars, nucleotides, pendent groups, fluorophores, lumiphores, radioactive molecules, lipids, fatty acids, derivatives thereof, or other groups known in the art. Illustratively, an inventive immunogen is conjugated to a protein.

An immunogen is optionally conjugated to a protein that promotes the immunogenicity of an immunogen, illustratively keyhole limpet hemocyanin (KLH), bovine serum albumin (BSA), or modifications thereof illustratively BLUE CARRIER immunogenic protein from Thermo Scientific, Rockford, Ill. Other sources of natural or artificial immunogenic protein conjugates are known in the art. Optionally, an immunogen is conjugated to an antibody. Optionally, an immunogen is conjugated to other regions of G-protein that may or may not also contain epitopes.

Several post-translational modifications are similarly envisioned as within the scope of the present invention illustratively including incorporation of a non-naturally occurring amino acid(s), phosphorylation, glycosylation, sulfation, and addition of pendent groups such as biotinylation, fluorophores, lumiphores, radioactive groups, antigens, or other molecules. Such modifications are also appreciated as encompassed by the term analogue.

It is appreciated that the inventive polypeptides, immunogens, or vaccines of the present invention are phosphorylated or unphosphorylated. RSV G protein is a naturally phosphorylated and glycosylated protein. Optionally, an immunogen is disulfide bonded. Disulfide bonds can be to amino acid residues within the sequence or to a second polypeptide or molecule.

RSV G protein fragments optionally have a single or multiple phosphorylations therein or other posttranslational modifications depending on particular amino acid substitutions. Methods of expressing and purifying natural or recombinant phosphoproteins or glycoproteins are known in the art. Illustratively, phosphoproteins and glycoproteins are recombinantly expressed in eukaryotic cells. Exemplary eukaryotic cells include yeast, HeLa cells, 293 cells, COS cells, Chinese hamster ovary cells (CHO), and many other cell types known in the art. Both eukaryotic and prokaryotic expression systems and cells are available illustratively from Invitrogen Corp., Carlsbad, Calif. It is appreciated that cell-free expression systems are similarly operable.

Optionally, the polypeptide is produced without glycosylation or phosphorylation. In a non-limiting example, polypeptides are synthesized in *E. coli* which is recognized in the art as incapable of properly glycosylating an expressed protein. It is appreciated that other synthetic means that do not glycosylate the polypeptide are similarly suitable. Thus, in this embodiment protein(s) are free from glycosylation.

Modifications and changes can be made in the structure of the polypeptides that are the subject of the application and still obtain a molecule having similar or improved characteristics as the wild-type sequence (e.g., a conservative amino acid substitution). For example, certain amino acids can be substituted for other amino acids in a sequence without appreciable loss of immunogenic activity. Because it is the interactive capacity and nature of a polypeptide that defines that polypeptide's biological functional activity, certain amino acid sequence substitutions can be made in a polypeptide sequence and nevertheless obtain a polypeptide with like or improved properties. Optionally, a polypeptide is used that has less or more immunogenic activity compared to the wild-type sequence.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is optionally used, those within ±1 are optionally used, and those within ±0.5 are optionally used.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitutions of amino acids whose hydrophilicity values are within ±2 are optionally used, those within ±1 are optionally used, and those within ±0.5 are optionally used.

Amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

Some embodiments of the present invention are compositions containing RSV G protein nucleic acid that can be expressed as encoded polypeptides or proteins. Optionally, nucleic acid sequences are those that encode polypeptides of SEQ ID NOs: 1-8. As the genetic code is degenerate and a person having ordinary skill in the art understands how to construct, isolate or otherwise identify a nucleic acid sequence that when expressed will produce a particular polypeptide sequence, any nucleic acid sequence that will produce the inventive polypeptides is within the scope of the present invention. The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino sequences. An exemplary nucleic acid sequence encoding RSV G protein is found within the gene sequence of accession number P03423. A person of ordinary skill in the art recognizes how to identify portions of the P03423 sequence that give rise to polypeptides of SEQ ID NOs: 1-4. Similarly, an exemplary nucleic acid sequence encoding RSV G protein is found within the gene sequence of accession number P20896. A person of ordinary skill in the art recognizes how to identify portions of the P20896 sequence that give rise to polypeptides of SEQ ID NOs: 6-7.

A nucleic acid as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding a peptide and/or polypeptide of this invention.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered cells" and "recombinant cells" are synonymous with "host cells" and are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. A host cell optionally does not possess a naturally occurring gene encoding RSV G protein. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide in accordance with the present invention one would illustratively prepare an expression vector that comprises a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* .chi. 1776 (ATCC No. 31537) as well as *E. coli* W3110 (F-, lambda-, prototrophic, ATCC No. 273325); bacilli such as *Bacillus subtilis*; and other enterobacteria such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage may also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica califormica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, Hep2, NIH3T3, RIN, Calu-3 and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, Adenovirus 5, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in $tk^-$, $hgprt^-$ or $aprt^-$ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

The nucleic acids encoding the peptides and polypeptides of this invention can also be administered as nucleic acid vaccines. For the purposes of vaccine delivery, a nucleic acid encoding a peptide or polypeptide of this invention can be in an expression vector that can comprise viral nucleic acid including, but not limited to, vaccinia virus, adenovirus, retrovirus and/or adeno-associated virus nucleic acid. The nucleic acid or vector of this invention can also be in a liposome or a delivery vehicle which can be taken up by a cell via receptor-mediated or other type of endocytosis. The nucleic acid vaccines of this invention can be in a pharmaceutically acceptable carrier or administered with an adjuvant. The nucleic acids encoding the peptides and polypeptides of this invention can also be administered to cells in vivo or ex vivo.

It is contemplated that the isolated nucleic acids or polypeptides of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural in transfected cells is indicative of overexpression, as is a relative abundance of the specific protein in relation to the other proteins produced by the host cell and, e.g., visible on a gel.

Further aspects of the present disclosure concern the isolation such as the purification, and in particular embodiments, the substantial purification, of an encoded isolated polypeptide or immunogen. The terms peptide or protein as used herein are synonymous with polypeptide or immunogen. The term "purified" or "isolated" polypeptide, peptide or protein as used herein, is intended to refer to a composition, isolatable from other components, wherein the protein or peptide is purified to any degree relative to its naturally-obtainable state, or its state as expressed in a cell, i.e., in this case, relative to its purity within a cell. An isolated protein or peptide, therefore, also refers to a protein or peptide, free from the environment in which it may naturally occur.

Generally, "purified" or "isolated" will refer to a protein or peptide composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of isolation of the protein or peptide will be known to those of skill in the art in light of the present disclosure and based on common knowledge in the art. These include, for example, determining the specific activity of an active fraction, or assessing the number of polypeptides within a fraction by SDS/PAGE analysis. A optional method for assessing the purity of a fraction is to calculate the specific activity of the fraction, to compare it to the specific activity of the initial extract, and to thus calculate the degree of purity, herein assessed by a "-fold purification number". The actual units used to represent the amount of purity will, of course, be dependent upon the particular assay technique chosen to follow the purification and whether or not the expressed protein or peptide exhibits a detectable activity or is otherwise recognizable such as via an ELISA assay.

Various techniques suitable for use in protein isolation will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxyapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially isolated protein or peptide.

There is no general requirement that the protein or peptide always be provided in their most isolated state. Indeed, it is contemplated that less substantially isolated products will have utility in certain embodiments. Partial isolation may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative isolation may have advantages in total recovery of protein product, or in maintaining the activity of an expressed protein.

It is known that the migration of a polypeptide can vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

The inventive method also illustratively includes isolation of inventive polypeptide from a host cell or host cell medium. Methods of protein isolation illustratively include column chromatography, affinity chromatography, gel electrophoresis, filtration, or other methods known in the art. An immunogen is optionally expressed with a tag operable for affinity purification. A tag is optionally a 6×His tag. A 6×His tagged inventive immunogen is illustratively isolated by Ni-NTA column chromatography or using an anti-6×His tag antibody fused to a solid support. (Geneway Biogech, San Diego, Calif.) Other tags and purification systems are similarly operable.

It is appreciated that an immunogen is optionally not tagged. In some embodiments isolation is optionally achieved by methods known in the art illustratively including ion-exchange chromatography, affinity chromatography, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

An immunogen or analogue thereof is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis and solution phase peptide synthesis or by the method of Hackeng, T M, et al., *Proc Natl Acad Sci USA*, 1997; 94(15):7845-50, the contents of which are incorporated herein by reference. Illustrative methods of chemical protein synthesis are reviewed by Miranda, L P, *Peptide Science*, 2000, 55:217-26 and Kochendoerfer G G, *Curr Opin Drug Discov Devel.* 2001; 4(2):205-14, the contents of which are incorporated herein by reference.

Immunogens are optionally characterized by measurements including, without limitation, western blot, macromolecular mass determinations by biophysical determinations, SDS-PAGE/staining, HPLC, ELISA, mass spectrometry, antibody recognition assays, cell viability assays, apoptosis assays, and assays to infer immune protection or immune pathology by adoptive transfer of cells, proteins or antibodies.

An immunogen is optionally modified to increase its immunogenicity. In a non-limiting example, the immunogen is coupled to chemical compounds or immunogenic carriers, provided that the coupling does not interfere with the desired biological activity of either the antigen or the carrier. Coupling is optionally by covalent association. For a review of some general considerations in coupling strategies, see Antibodies, A Laboratory Manual, Cold Spring Harbor Laboratory, ed. E. Harlow and D. Lane (1988), the contents of which are incorporated herein by reference. Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads;

activated carbon; or bentonite. Useful chemical compounds for coupling include, without limitation, dinitrophenol groups and arsonilic acid.

An immunogen may also be modified by other techniques, illustratively including denaturation with heat and/or SDS.

An immunogen of the present invention may also be used in the form of a pharmaceutically acceptable salt. Suitable acids and bases which are capable of forming salts with the immunogens of the present invention are well known to those of skill in the art, and include inorganic and organic acids and bases.

In another aspect, the invention provides a multi-component vaccine. Optionally, a multi-component vaccine contains more than one immunogen. An inventive vaccine optionally contains 2, 3, 4, 5, 6, 7, 8, 9, 10, or more immunogens in a single vaccine. Optionally, a first immunogen is a polypeptide corresponding to amino acid position 164 to amino acid position 176 of SEQ ID NO: 1 (RSVA2 strain), or an analogue thereof. Optionally, a first immunogen is a polypeptide corresponding to amino acid position 163 to amino acid position 190 of SEQ ID NOs: 1, 7 (RSV B_18537), 8 (RSVGA_CH17), or analogues thereof. It is appreciated that any of the aforementioned modifications, mutations, or alterations stated herein or otherwise known in the art are operable as to the inventive immunogens of the present invention. Optionally, a first immunogen is a polypeptide of SEQ ID NO: 2 (RSVGA_A2).

An optional second immunogen is a polypeptide corresponding to amino acid position 155 to amino acid position 206 of SEQ ID NO: 1 or an analogue thereof or to amino acid position 163 to amino acid position 190 of SEQ ID NOs: 1, 7, 8, or an analogue thereof. Optionally, the first and the second immunogens differ by at least one atom. Optionally, the second immunogen is a longer or shorter polypeptide than the first immunogen. Optionally, the first and second immunogens confer unique but possibly overlapping immunogenic characteristics.

Optionally, the second immunogen is a polypeptide of SEQ ID NOs: 3 (RSVGA_A2), 4 (RSVGA_A2), 5 (RSVGA_CH17), or 6 (RSVGB). Alternatively, the second immunogen is an analogue of SEQ ID NOs: 3, 4, 5, or 6.

An inventive vaccine is optionally a multicomponent vaccine of two immunogens such as the immunogen of amino acid position 163 to amino acid position 190 of SEQ ID NOs: 1 or 7, or an analogue thereof and a second immunogen corresponding to amino acid position 155 to amino acid position 206 of SEQ ID NO: 1 or an analogue thereof.

It is further appreciated that the first, second, or first and second immunogens, or other polypeptides of the present invention are optionally within a vaccine that contains other immunogens. Illustratively, other immunogens include the immunogens of SEQ ID NOs. 2, 3, 4, 5, 6, or the RSV F protein or an analogue thereof. The entire RSV F protein sequence need not be present. A fragment of the RSV F protein operable to induce an immune response is operable as a component of a multi-component vaccine. It is appreciated that the immunogen related to the F protein sequence may be an analogue thereof. It is appreciated that in some embodiments a vaccine is free of RSV F protein or an analogue thereof, e.g. RSV F protein or an analogue thereof is optionally absent from a vaccine.

The first and second immunogens are optionally separately expressed, isolated and formulated as separate polypeptides and subsequently combined to form as single vaccine for administration by a single dose or other dosing schedule operable to induce a protective immune response in a subject.

Alternatively, the first and second immunogen are co-expressed in the same host cell. Co-expression is optionally by expression of individual polypeptide sequences on the same or different expression vectors. The polypeptides are optionally co-expressed by simultaneous expression in a host cell, or are differentially expressed by exposing the host cell to different conditions to express one polypeptide while maintaining the coding sequence for the other in a non-expressive state. The resulting expressed polypeptides are simultaneously or differentially purified or otherwise made suitable for administration.

Optionally, the first and second immunogens are present in the same expression system. The first and second immunogens are optionally associated by a linker. A linker is optionally an intermediate polypeptide fragment. Optionally, the nucleic acid sequence encoding the first and second immunogens are linked by a ribosome binding site. As such each gene may be present on a single plasmid or other expression system and be simultaneously or differentially expressed.

Where the first and second immunogens are liked by a linker that is a polypeptide sequence or partial polypeptide sequence, the intermediate sequence is optionally excisable. Intermediate or terminal protein or peptide excision is performed by methods known in the art. Illustratively, excision is performed by a protease cleavage. A protease is optionally, factor Xa, thrombin, or other substantially specific protease known in the art. A protease optionally recognizes a single or two sites within a linker.

Optionally, an inventive vaccine contains an adjuvant. Suitable adjuvants illustratively include dimethyl dioctadecyl-ammonium bromide (DDA); monophosphoryl lipid A (MPL); LTK63, lipophilic quaternary ammonium salt-DDA, DDA-MPL, aluminum salts, aluminum hydroxide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles illustratively including calcium phosphate nanoparticles, combination of soybean oil, emulsifying agents, and ethanol to form a nanoemulsion; AS04, ZADAXIN, or combinations thereof.

An immunogen is optionally delivered as naked polypeptide, naked nucleotide, in aqueous solution, in an emulsion, or in other suitable delivery compositions. In some embodiments an immunogen is delivered as a vaccine or as a vaccine component of a pharmaceutical package. Optionally, a vaccine (or multiple vaccines) is present in an emulsion comprised of suitable emulsification agents. Optionally, a multi-component vaccine is emulsified. Optionally, a single subunit vaccine is emulsified. Suitable emulsification agents illustratively include supramolecular biovectors (SMBV), nanoparticles such as described by Major, M, et al, *Biochim. Biophys. Acta*, 1997; 1327:32-40, De Migel, I, et al, *Pharm. Res.*, 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et el, *Vaccine*, 1996; 14:1353-1360, Prieur, E., et al, *Vaccine*, 1996; 14:511-520, Baudner B, et al, *Infect Immun*, 2002; 70:4785-4790; Liposomes such as described by El Guink et al., *Vaccine*, 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally, the adjuvant is monophosphoryl lipid A.

The proteins and nucleic acid sequences of the invention, alone or in combination with other antigens, antibodies or nucleic acid sequences may further be used in therapeutic compositions and in methods for treating humans and/or animals with RSV infection. For example, one such therapeutic composition may be formulated to contain a carrier or diluent and one or more RSV immunogens of the invention. The therapeutic composition illustratively contains an inventive RSV protein, nucleic acid sequence, or analogue thereof as described herein and a suitable pharmaceutical carrier. Optionally, a therapeutic composition contains an RSV G protein fragment of SEQ ID NOs: 1-7. Optionally, a therapeutic composition is a multi-component vaccine. A multi-component vaccine optionally contains an immunogen with the polypeptide sequence of SEQ ID NOs: 2, 4, 5, or 6 and a second immunogen of polypeptide sequence SEQ ID NO: 3.

Suitable pharmaceutically acceptable carriers facilitate administration of the proteins but are physiologically inert and/or non-harmful. Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the inventive composition contains conventional pharmaceutical ingredients, such as preservatives, or chemical stabilizers. Suitable ingredients operable herein include, for example, casamino acids, sucrose, gelatin, phenol red, N—Z amine, monopotassium diphosphate, lactose, lactalbumin hydrolysate, and dried milk.

Alternatively, or in addition to the RSV immunogens of the present invention, other agents useful in treating RSV infection, e.g., antivirals or immunostimulatory agents are expected to be useful in reducing or eliminating disease symptoms. Agents operable herein optionally act to assist the natural immunity of the infected human or animal. Thus, such agents may operate in concert with the therapeutic compositions of this invention. The development of therapeutic compositions containing these agents is within the skill of one in the art and in view of the teachings of this invention.

Immunological compositions and other pharmaceutical compositions containing the immunogen(s) described herein are included within the scope of the present invention. One or more of these compositions can be formulated and packaged, alone or in combination, using methods and materials known to those skilled in the art for vaccines. The immunological response may be therapeutic or prophylactic and may provide antibody immunity or cellular immunity such as that produced by T lymphocytes such as cytotoxic T lymphocytes or $CD4^+$ T lymphocytes.

To enhance immunogenicity, the inventive vaccines or immunogens can be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 Daltons, and optionally of greater than 10,000 Daltons. Carrier molecules often contain a reactive group to facilitate covalent conjugation to a hapten. The carboxylic acid group or amine group of amino acids or the sugar groups of glycoproteins are often used in this manner. Carriers lacking such groups can often be reacted with appropriate chemicals to produce them. Optionally, an immune response is produced when the immunogen is injected into animals such as humans, primates, mice, rabbits, rats, goats, sheep, guinea pigs, chickens, and other animals, optionally mice and humans. Alternatively, a multiple antigenic peptide comprising multiple copies of an immunogen, or an antigenically or immunologically equivalent immunogen may be sufficiently antigenic to improve immunogenicity without the use of a carrier.

The inventive vaccines and immunogens are optionally administered with an adjuvant. Optionally an adjuvant is alum (aluminum phosphate or aluminum hydroxide). Chemically defined preparations such as muramyl dipeptide, monophosphoryl lipid A, phospholipid conjugates, encapsulation of the conjugate within a proteoliposome, and encapsulation of the protein in lipid vesicles are also operable with the present invention.

Methods for treating individuals diagnosed with RSV disease and conditions associated with RSV infection, such as bronchiolitis, upper respiratory infection, and lower respiratory infection by administering the compositions described herein are also provided in this invention.

Also provided are methods creating an immune response in a subject or methods of treating or preventing an RSV infection in a subject comprising administering to the subject an effective amount of vaccine, immunogen, molecule, antibody or peptide-encoding nucleic acid of the invention. Optionally, a vaccine includes the immunogen of SEQ ID NOs: 2, 3, 4, 5, or 6, or a combination of multiple polypeptides of SEQ ID NOs: 2, 3, 4, 5, or 6.

As used herein the term "immune response" means the increase or decrease in a physiological response to an antigen in a subject. Illustrative immune responses include, but are not limited to reduction in leukocyte trafficking, activation of T-cells, activation of cytotoxic T lymphocytes, modulating populations of $CD4^+$ cells, $CD11b^+$ cells, NK cells, $DX5^+$ cells, $B220^+$ cells, or $RB6-8C5^+$ PMN cells, altering virus clearance rate, altering leukocyte trafficking, altering interferon gamma (IFN-γ) production, decreasing virus replication rate, or other immune responses recognized in the art. An immune response is a protective immune response if any immune response prevents infection by RSV, provides RSV clearance, prevents RSV entry into a cell, or other prevention recognized in the art.

The inventive method also provides administering a second vaccine. A second vaccine optionally includes a polypeptide corresponding to amino acid position 155 to amino acid position 206 of SEQ ID NO: 1 or an analogue thereof. Optionally, a second vaccine includes an immunogen with the amino acid sequence of SEQ ID NOs: 2-6. Optionally, a second vaccine is a multi-component vaccine that has two or more immunogens. Optionally, a second vaccine includes the immunogens of any of SEQ ID NOs: 3-6. Optionally, a first or second vaccine is RSV. Optionally, a first or second vaccine is formalin inactivated RSV A2 or other inactivated strain. Optionally a first or second vaccine or immunogen is not a virus The second vaccine is optionally administered simultaneous with a first vaccine. Optionally, the second vaccine is administered prior to or subsequent to the first vaccine.

Figure 4:
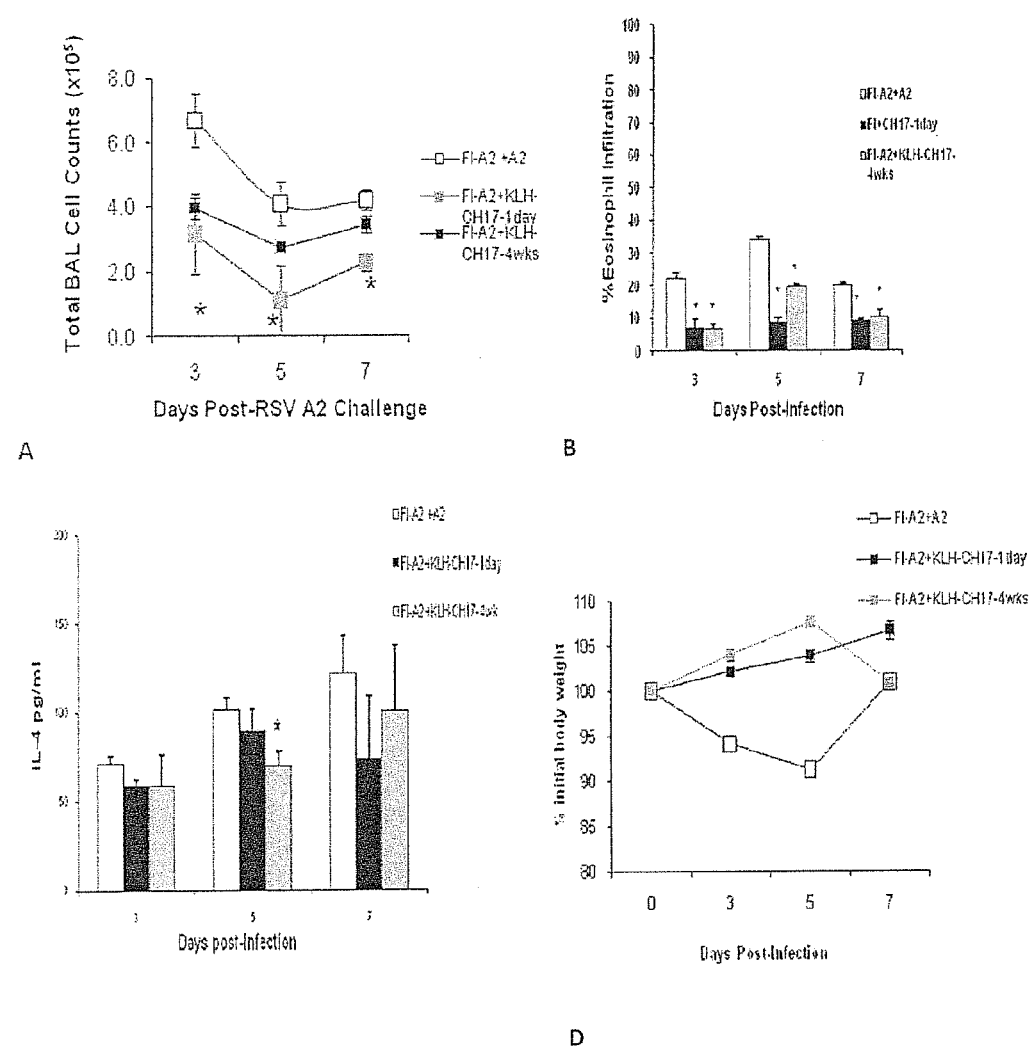
FIG. 4 represents the total cell content of BAL fluid (A), eosinophil levels in BAL (B), IL-4 content in BAL fluid (C) and weight loss (D) in mice challenged with RSV following immunization with FI-A2 and vaccines from RSVGA-CH17 (SEQ ID NO. 5)
Figure 5:
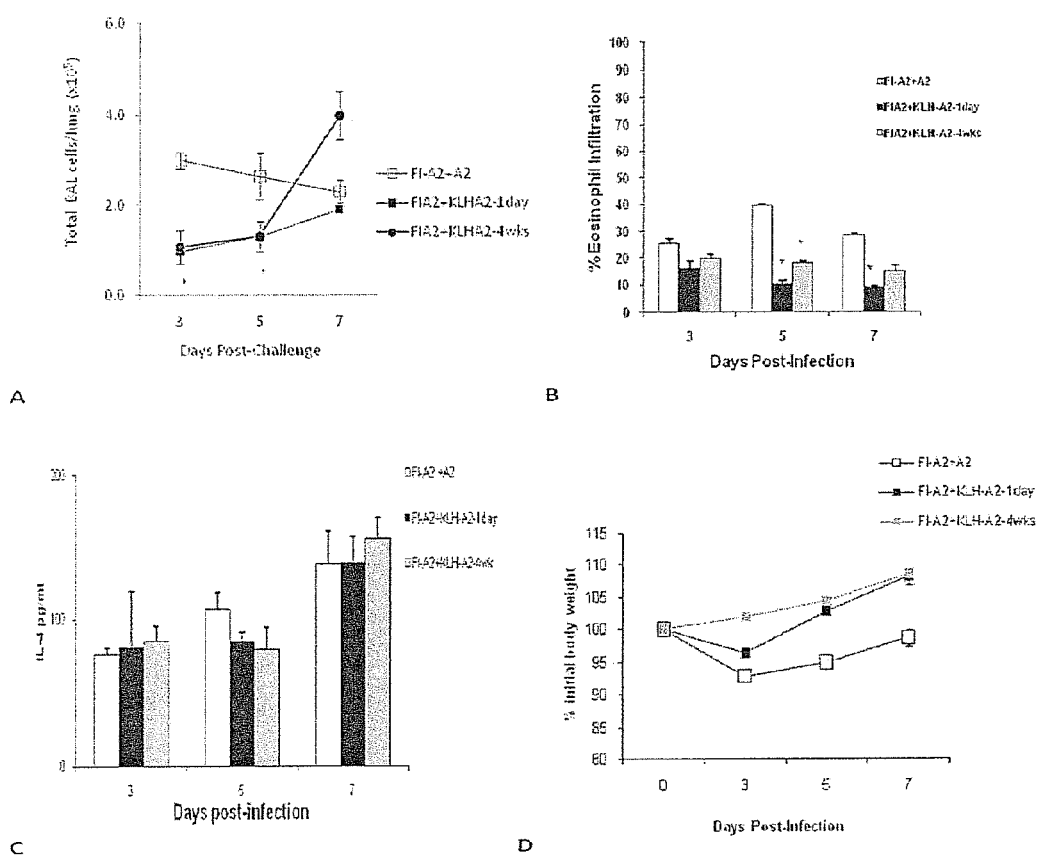
FIG. 5 represents the total cell content of BAL fluid (A), eosinophil levels in BAL (B), IL-4 content in BAL fluid (C) and weight loss (D) in mice following RSV challenge after being immunized with FI-A2 and vaccines derived from RSVGA-A2 (SEQ ID NO. 4).

Prior vaccines for RSV suffered numerous negative side effects including an increase in the severity of RSV associated disease subsequent to administration of a formalin inactivated vaccine in young children. Associated with enhanced disease after prior attenuated RSV vaccine administration is the increase in eosinophils in pulmonary tissue. Haynes, L., et al., *J Virol*, 2003; 77:9831-9844. Antibodies directed toward epitope regions in RSV G-protein or developed following vaccination with the inventive vaccine(s) decrease pulmonary eosinophilia after RSV infection in subjects suggesting improved safety and efficacy when combined with traditional formalin attenuated RSV vaccine. (e.g. FIG. 4 or 5) Thus, in some embodiments of the present invention is prior, simultaneous, or subsequent administration of the inventive vaccine(s) with other RSV vaccines.

The invention is optionally delivered with, prior to, or subsequent to an anti-viral composition. Anti-viral compositions illustratively include small drug-like molecule inhibitors of RSV replication and infection, nucleoside analogs such as ribavarin, EICAR, Pyrazofurin, 3-deazaguanine, GR92938X and LY253963. These inhibitors are targeted to inhibit inosine monophosphate dehydrogenase (IMPDH). Inhibitors targeted to inhibit virus adsorption and entry are also useful herein. Illustratively among this class are polyoxometalates and CL387626 (Wyeth-Ayerst, Pearl River, N.Y.). Other examples of polyoxometalates are T118, Trimeris'benzathrone, BABIM and RD30028. Antisense oligonucleotide inhibitors of RSV are also useful, such as V590, an inhibitor that targets residues in RSV NS1/NS2 genes.

Immunogens are optionally incorporated into a pharmaceutical carrier such as saline, dextrose, water, glycerol, ethanol, other therapeutic compounds, and combinations thereof. The formulation should be appropriate for the mode of administration and may include other immune modifiers such as heparin. The composition may also contain other additional biologically inert ingredients such as flavorants, fillers, etc.

Suitable methods of administration include, but are not limited to intramuscular, intravenous, intranasal, mucosal, oral, parenteral, intravaginal, transdermal, via aerosol delivery or by any route that produces the desired biological effect or immune response.

A vaccine of the invention is optionally packaged in a single dosage for immunization by parenteral (i.e., intramuscular, intradermal or subcutaneous) administration or nasopharyngeal (i.e., intranasal) administration. The vaccine is optionally delivered by inhalation. The vaccine is optionally combined with a pharmaceutically acceptable carrier to facilitate administration. The carrier is usually water or a buffered saline, with or without a preservative. The vaccine may be lyophilized for resuspension at the time of administration or in solution.

Optional microencapsulation of the inventive vaccine will also provide a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that may be considered. Examples of useful polymers illustratively include polycarbonates, polyesters, polyurethanes, polyorthoesters polyamides, poly (d,l-lactide-co-glycolide) (PLGA) and other biodegradable polymers.

The inventive vaccine may additionally contain stabilizers such as thimerosal (ethyl(2-mercaptobenzoate-S)mercury sodium salt) (Sigma Chemical Company, St. Louis, Mo.) or physiologically acceptable preservatives.

According to the method of the invention, a human or an animal may be treated for for RSV, other viral infection or bacterial infection by administering an effective amount of an inventive vaccine. Optionally, a vaccine is administered prophylactically. An "effective amount" is an amount that will induce an immune response in a subject. Illustratively, an effective amount of the compositions of this invention ranges from nanogram/kg to milligram/kg amounts for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician or veterinarian and methods for determining dose amounts and regimens and preparing dosage forms are described, for example, in Remington's Pharmaceutical Sciences, (Martin, E. W., ed., latest edition), Mack Publishing Co., Easton, Pa. Optionally, a single administration is operable to induce an immune response.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley and Sons, New York, N.Y.; and manufacturer's literature on use of protein purification products known to those of skill in the art.

Assays for neural cell biological activities are described, e.g., in Wouterlood (ed. 1995) Neuroscience Protocols modules 10, Elsevier; Methods in Neurosciences Academic Press; and Neuromethods Humana Press, Totowa, N.J.

FACS analyses are illustratively described in Melamed, et al. (1990) Flow Cytometry and Sorting Wiley-Liss, Inc., New York, N.Y.; Shapiro (1988) Practical Flow Cytometry Liss, New York, N.Y.; and Robinson, et al. (1993) Handbook of Flow Cytometry Methods Wiley-Liss, New York, N.Y.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian tissue, specifically, analyses of mouse tissue, a person having ordinary skill in the art recognizes that similar techniques and other techniques known in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained. Variations within the concepts of the invention are apparent to those skilled in the art. Additional reagents, and preparation of proteins such as immunogens, cells, etc, are illustratively found in WO 97/27299 and U.S. Publication No. 2006-0018925, the contents of each of which are incorporated herein by reference.

EXAMPLE 1

Preparation of Immunogens

RSV G protein immunogens are prepared as pharmaceutical compositions with a pharmaceutically acceptable carrier, excipient or diluent. For example, the RSV G protein sequences described herein and encoded by nucleic acid contained in modified pET-32-LIC plasmids are expressed as thioredoxin (Trx)-fusion proteins in transformed *E. coli* BL21/DE3 cells following induction with IPTG. All Trx-fusion proteins are recovered from transformed cell pellets by extraction with 8M urea, followed by affinity purification using TALON® (Clontech, Palo Alto, Calif.) and dialysis against PBS. Purified Trx-RSV G polypeptides are freed from contaminating endotoxin by treatment with polymyxin B beads (BioRad, Hercules, Calif.). Details and modifications of this procedure are well known to those of ordinary skill in the art. Upon use for immunization, immunogens are further combined or admixed with an adjuvant, such as alum or a proteosome-based adjuvant.

Alternatively, immunogens are synthesized using a simultaneous, multiple solid-phase peptide synthesis method on a peptide synthesizer (Perkin-Elmer Applied Biosystems, Berkeley, Calif.), and tested for homogeneity by reverse-phase liquid chromatography and capillary electrophoresis.

Immunogens are assayed for their ability to bind CX3C receptor types by determination of cell adherence. A pcDNA 3.1 plasmid containing the CX3CR1 gene and a neomycin resistance gene is stably transfected into human embryonic kidney (HEK) cells. Neomycin resistance is used for selection and maintenance of plasmid transfection of human embryonic kidney cells. To confirm transfection, lysates of CX3CR1-transfected HEK cells are stained with anti-CX3CR1 antibody in western blot analysis or intact transfected cells are examined by flow cytometry. Purified $^{125}$I-G glycoprotein is examined for binding to 293-CX3CR1 cells essentially as described in Combadiere, C., et al., *J. Biol. Chem.*, 1998; 273:23799-23804, the contents of which are incorporated herein by reference. Purified $^{125}$I-G glycoprotein in binding buffer (Hanks' buffered saline solution with 1 mg/ml bovine serum albumin and 0.01% azide, pH 7.4, final volume 200 µl) is incubated with $10^6$ CX3CR1-transfected HEK cells in the absence of or presence of varying concentrations of unlabeled immunogen of either a wild-type sequence or analogue sequence. After 2 hours at room temperature the cells are washed with one ml of binding medium. The presence of wild-type G-glycoprotein immunogen sequence effectively competes with $^{125}$I-G glycoprotein binding to cells as revealed by reduced gamma emissions from the cell pellet following washing. The presence of analogue sequences shows altered competition indicating alteration in CX3C receptor binding by the analogue relative to the wild-type sequence.

EXAMPLE 2

Preparation of RSV

The A2 strain of RSV is propagated in Vero cells (ATCC CCL 881) essentially as described in Tripp, R A, et al, *J. Virol.* 1999; 73:7099-107. Briefly, Vero cells are maintained in DMEM (GIBCO Laboratories, Grand Island, N.Y.) supplemented with 2% heat-inactivated (56° C.) fetal bovine serum (FBS; HyClone Laboratories, Salt Lake City, Utah), 1% L-glutamine, and 1% antibiotic-antimycotic (all from GIBCO) (TCM). Upon detectable cytopathic effect, the TCM is decanted and replaced with a minimal volume of Dulbecco's modified phosphate-buffered saline (D-PBS) and frozen at −70° C. The flask is thawed, and the loosely adherent cell monolayer is scraped off with a cell scraper (Costar, Cambridge, Mass.) and collected. The cells and supernatant are frozen at −70° C., thawed, and then centrifuged at 2,000×g for 15 min at 4° C. The virus titer is determined by methylcellulose plaque assay on Vero cells.

EXAMPLE 3

Subject Anti-RSV G Monoclonal Antibody Treatment

Eight- to ten-week old, specific-pathogen-free, female BALB/c mice (The Jackson Laboratories) are used as subjects for studies. Mice are housed in micro-isolator cages and fed sterilized water and food ad libitum. All studies are performed in accordance with the guidelines of the Institutional Animal Care and Use Committee.

Mice are anesthetized by intraperitoeal (i.p.) administration of Avertin (2% 2,2,2-tribromoethanol, 2% tert-amyl-alcohol, 180-250 mg/kg), and intranasal (i.n.) challenged with $10^6$ PFU of RSV in serum-free DMEM (50 µl volume). Three days post-infection (p.i.) mice are given by i.p. administration 150 µg (low dose)-300 µg (high dose) per mouse of anti-G glycoprotein (131-2G, endotoxin <5 EU/mg) monoclonal antibody or control normal mouse IgG (Pierce). No fewer than three mice per treatment are examined per time point.

EXAMPLE 4

Anti-RSV G mAb Treatment Reduces Pulmonary Leukocyte Infiltration

RSV infected mice are treated (as described in Example 3) with either the control normal mouse IgG or anti-RSV G monoclonal antibody are analyzed for pulmonary leukocyte trafficking as described by Haynes L M, et al, *J. Infec. Dis.*, 2009, 200(3):439-447. Briefly, mice are anesthetized with Avertin (2,2,2 tribromoethanol) and exsanguinated by severing the right brachial artery. Bronchoalveolar leukocyte cells are harvested by lavaging the lungs three times with 1 ml Dulbecco's PBS. BAL cells are washed in Dulbecco's PBS (GIBCO) containing 1% bovine serum albumin (Sigma-Aldrich, St. Louis, Mo.) and then stained (4° C., 30 min) with an appropriate dilution of fluorescein isothiocyanate (FITC)-, allophycocyanin (APC)-, or phycoerythrin (PE)-conjugated anti-CD3ε (145-2C11), anti-CD45R/B220 (RA3-6B2), anti-CD8 (Ly-2), anti-neutrophil (PMN) (RB6-8C5), anti-CD11b (M1/70) antibodies or isotype antibody controls (BDBiosciences, Inc.).

Anti-G antibody treatment correlates with significant reduction in pulmonary leukocyte trafficking and titer of virus in the lung compared to control treated mice by day 5 post-infection. By day 7 post-infection, the level of pulmonary infiltration in treated mice continues to exhibit significantly reduced pulmonary cell infiltration.

The alveolar inflammatory cell types affected by anti-G monoclonal antibody treatment and the bronchoalveolar lavage (BAL) cell subsets are determined at several time points post-treatment (Table 1) Immunization is linked to a marked reduction in CD4+ and CD11b+ cell trafficking, and with modest decreases in CD8+, DX5+ NK, and RB6-8C5+ PMN cells in the BAL cell population on day 5 p.i. By day 7 p.i., immunization decreases the numbers of all cell subsets examined.

TABLE 1 nIg represents control normal mouse IgG treated mice and anti-G represents mice treated with anti-RSV G antibodies.

| Day p.i. | Phenotype[b] | nIg | anti-G (300 ug) | % Reduction |
|---|---|---|---|---|
| 5 | CD8 | 5632 ± 667 | 3240 ± 437 | 42 |
|  | CD4 | 4347 ± 514 | 1520 ± 205* | 65 |
|  | B220 | 1778 ± 210 | 880 ± 118* | 51 |
|  | DX5 | 4644 ± 549 | 2760 ± 373 | 41 |
|  | CD11b | 5138 ± 608 | 1840 ± 248* | 64 |
|  | PMN | 2470 ± 292 | 1080 ± 145* | 56 |
| 7 | CD8 | 7054 ± 879 | 2415 ± 445* | 66 |
|  | CD4 | 4023 ± 501 | 1120 ± 206* | 72 |
|  | B220 | 3790 ± 472 | 1190 ± 219* | 69 |
|  | DX5 | 6355 ± 791 | 2275 ± 419* | 64 |
|  | CD11b | 8512 ± 1060 | 2975 ± 548* | 65 |
|  | PMN | 1224 ± 153 | 630 ± 116 | 49 | p.i. represents days post infection.

EXAMPLE 5

Anti-G Antibody Treatment Reduces Post-Infection IFNγ Levels in the Lung

Figure 1B:
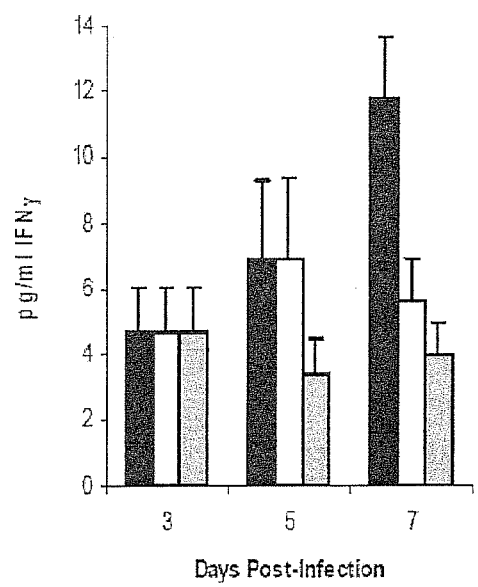
Figure 2:
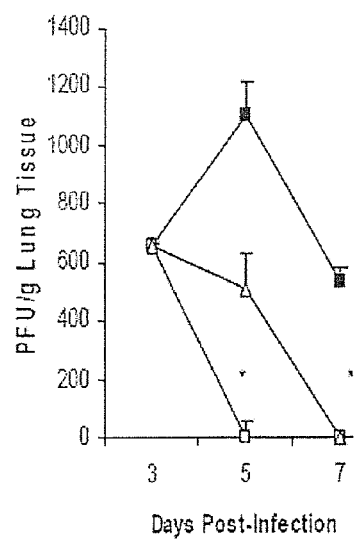
FIG. 2 represents virus titer reductions in mice challenged with RSV that were treated or not treated with antibodies that bind the G protein similar to those induced by the inventive immunogens after RSV infection where solid squares represent control antibody treated mice, open triangles represent anti-RSV G antibody treated (low-dose) mice, and the open squares represent anti-RSV G antibody treated (high-dose) treated mice.
Figure 3:
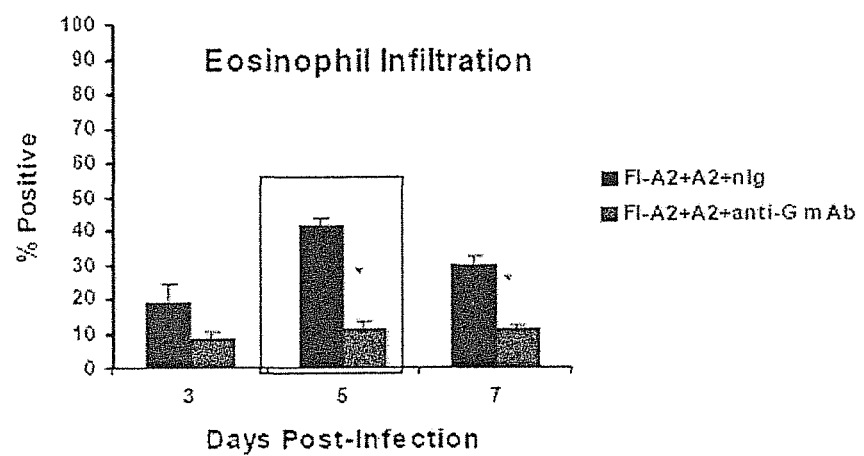
FIG. 3 represents reduction in pulmonary eosinophilia in formalin-inactivated-RSV A2 (FI-A2) vaccinated mice challenged with RSV following prophalytic treatment, or not, with antibodies that bind the G protein similar to those induced by the inventive immunogen after RSV challenge.

Mouse lungs are analyzed for IL-4 and IFNγ levels in cell-free bronchoalveolar lavage (BAL) fluid using a capture enzyme-linked immunoassay kit per manufacturer's instructions (eBiosciences, San Diego, Calif.). Antibody treatment is not associated with differences in the low levels of IL-4 (FIG. 1A). In contrast, antibody treatment markedly decreases IFNγ levels in cell-free BAL supernatants (FIG. 1B).

EXAMPLE 6

RSV Levels are Reduced by Antibodies Given Following RSV Infection

Serum from individual mice is collected 14 days after the second of two subcutaneous administrations of an immunogen in alum, as described in Example 3. Aliquots of pre-titered RSV are mixed with serially diluted samples of individual mouse sera and incubated for 1 hr at room temperature and assayed for RSV neutralizing antibodies by plaque reduction assay. Mixtures are applied in duplicate to 24-well plates containing 60-80% confluent monolayers of HEp-2 or Vero cells, adsorbed for 90 minutes at 4° C., followed by washing and incubation of the plates for 40 h at 37° C. in 1 ml of RPMI medium supplemented with 1% fetal calf serum. After incubation, the monolayers are fixed with 15% formaldehyde or 80:20 acetone:PBS and stained with 0.01% crystal violet or immunostaining for visualization of viral plaques. Plaque reduction is calculated as the plaque reduction neutralization titer$_{50}$ (PRNT$_{50}$), which is the reciprocal dilution of sera required to neutralize 50% of RSV plaques on a sub-confluent monolayer of HEp-2 or Vero cells. Immunization with either the 164-176 RSV G region polypeptide or the multicomponent vaccine incorporating the 163-190 RSV G region polypeptide along with the 155-206 RSV G region polypeptide demonstrate strong neutralizing antibody responses.

EXAMPLE 7

RSV Titer Reduction in Antibody Treated Mice

Virus titers in the lungs of RSV-infected mice are determined as previously described by Sullender, W, *Virology*, 1995; 209:70-79. Briefly, lungs are aseptically removed from 3-4 mice per group at days 3, 5, 7 or 11 p.i. and stored at −70° C. until assay. Lungs are weighed and individual lung samples homogenized in 1 ml of cold, sterile Dulbecco's PBS (GIBCO), and ten-fold serial dilutions (in serum free DMEM) of the lung homogenates are added to confluent Vero cell monolayers in 24 well plates. Following adsorption for 2 hours at 37° C., cell monolayers are overlaid with tissue culture media DMEM (GIBCO) containing 10% FBS (Hyclone, Logan, Utah), incubated at 37° C. for 3-4 days and then enumerated by immunostaining with monoclonal antibodies against the G and F proteins (232-1F, 130-6D and 131-2A, respectively).

On day 5 post-infection, which corresponds to the peak of viral replication in this model, there is a marked decrease ($P<0.016$) in virus titers in immunized mice, and by day 7 the levels of virus are below the limits of detection (FIG. 2).

EXAMPLE 8

Pulmonary Eosinophilia Reduction in Anti-RSV G Monoclonal Antibody Treated FI-A2 Immunized Mice Mice (6-8 wks old) are immunized with $10^6$ PFU equivalents of formalin-inactivated RSV/A2 (FI-A2) in the superficial gluteal muscle and rested for four weeks. One day prior to challenge with $10^6$ PFU live RSV, mice are given by i.p. administration 300 μg per mouse of anti-G glycoprotein (131-2G, endotoxin <5 EU/mg) monoclonal antibody or control normal mouse IgG (Pierce) (as described in Example 3). Induction of eosinophilia is determined according to procedures described in Mader et al. *Vaccine* 18:1110, 2000. Treatment with anti-RSV G monoclonal antibody (131-2G) protects mice against RSV challenge. Interestingly, at the peak of inflammation (day 5 p.i.), the levels of pulmonary eosinophilia are much reduced compared to control antibody treated mice (FIG. 3).

EXAMPLE 9

G-Protein Immunization Prevents FI-A2 Induced Toxicity

Eight- to ten-week old, specific-pathogen-free, female BALB/c mice (The Jackson Laboratories) are used as subjects for immunization. Mice are housed in micro-isolator cages and fed sterilized water and food ad libitum. All studies are performed in accordance with the guidelines of the Institutional Animal Care and Use Committee.

Immunization with this G polypeptide will induce anti-G antibodies that act similarly to anti-G monoclonal antibodies as described in Example 3 and inhibit pulmonary disease associated with FI-RSV immunization. Mice (6-8 wks old) are 1) immunized with $10^6$ PFU equivalents of formalin-inactivated RSV/A2 (FI-A2) in the superficial gluteal muscle, rested for 24 hrs and then 1) subcutaneously immunized on the hind limb with KLH conjugated RSV CH17 peptide (aa163-190; SEQ ID NO. 5) (FI-A2+KLH-CH17-1 day) (10 µg protein in a volume of 50 µl PBS/Titermax); 2) rested for four weeks and then immunized with KLH-RSV CH17 peptide (FI-A2+KLH-CH17-4 wks) (10 µg protein in a volume of 50 µl PBS/Titermax); or 3) boosted at equivalent times with PBS control (50 µL). Two to three weeks after peptide immunization, both peptide boosted groups are intraperitoneally boosted with KLH-CH17 in PBS.

Two weeks following the second peptide boost, groups are challenged intranasally with $10^6$ PFU live RSV A2 in serum-free DMEM (50 µl volume), and total bronchoalveolar lavage (BAL) cells (FIG. 4A), eosinophil infiltration (FIG. 4B), IL-4 cytokine production (FIG. 4C) and body weights (FIG. 4D) are determined. No fewer than three mice per treatment are examined per time point.

Mice boosted either at day 1 or four weeks following immunization with F1-A2 show significantly reduced total cell counts in lavage fluid (FIG. 4A) at 3, 5, and 7 days post RSV challenge. Correspondingly, eosinophilia is statistically significantly reduced at all three analyses days (FIG. 4B). IL-4 levels trend toward reduced levels with statistical significance observed at day 5 in the four week boost group (FIG. 4C). An important marker for disease severity is observed in FIG. 4D where FI-A2 alone immunized mice demonstrate as much as 10% weight loss in by 5 days post-challenge. Boosting at either day 1 or four weeks following FI-A2, prevents weight loss in the same time period.

EXAMPLE 10

A Second G-Protein Sequence Prevents F1-A2 Induced Toxicity

Mice (6-8 wks old) are 1) immunized with $10^6$ PFU equivalents of formalin-inactivated RSV/A2 (FI-A2) in the superficial gluteal muscle, rested for 24 hrs and then 1) subcutaneously immunized on the hind limb with KLH conjugated RSV A2peptide (SEQ ID NO: 4) (FI-A2+KLH-A2-1 day) (10 µg protein in a volume of 50 µl PBS/alum); 2) rested for four weeks and then immunized with KLH-RSV A2peptide (FI-A2+KLH-A2-4 wks) (10 µg protein in a volume of 50 µl PBS/alum); or 3) boosted at equivalent times with PBS control (50 µL). Two to three weeks after peptide immunization, both peptide boosted groups are intraperitoneally boosted with KLH-A2 in PBS.

Two weeks following the second peptide boost, groups are challenged intranasally with $10^6$ PFU live RSV A2 in serum-free DMEM (50 µl volume), and total bronchoalveolar lavage (BAL) cells (FIG. 4A), eosinophil infiltration (FIG. 4B), IL-4 cytokine production (FIG. 4C) and body weights (FIG. 4D) are determined. No fewer than three mice per treatment are examined per time point.

Similar to the results observed following boosting with CH17 (SEQ ID NO: 5) of Example 9, mice boosted either at day 1 or four weeks with KLH-A2 (SEQ ID NO: 4) following immunization with F1-A2 show significantly reduced total cell counts in lavage fluid (FIG. 5A) at 3 and 5 days post RSV challenge. Correspondingly, eosinophilia is statistically significantly reduced at all three analyses days (FIG. 5B). IL-4 levels trend toward reduced levels (FIG. 5C). Organismal disease severity is reduced relative to the weight loss observed in the F1-A2 immunized group where boosting at four weeks following FI-A2 produced no weight loss in days 3-7. Mice boosted at day 1 showed mild weight loss at day 3 that reversed to modest weight gain by day 7 indicating more rapid recovery.

EXAMPLE 11

Immunization with RSV B Strain G-Protein Peptide aa155-206 Induces Decreased Disease Severity with Reduced F1-A2 Induced Toxicity Mice are immunized as in Example 9 with B strain G-protein peptide aa155-206 (SEQ ID NO: 6) and challenged with RSV-A2 strain as in Example 4 or RSV-B1 strain. Although the RSV B G-protein has a unique sequence relative to the A strains, immunization with the peptide of SEQ ID NO: 6 demonstrates reduced levels of pulmonary eosinophilia compared to prior immunization attempts with alternate vaccines. In measurements of disease severity as in Example 8 and 9, immunization with SEQ ID NO: 6 also reduces weight loss and IL-4 levels relative to control mice. Also, similar to immunization with SEQ ID NO: 4, mice immunized with the peptide corresponding to the B strain (SEQ ID NO: 6) demonstrate similar reductions in inflammatory bronchoalveolar lavage (BAL) cell subsets determined at several time points post-treatment. Immunization is linked to a marked reduction in $CD4^+$ and $CD11b^+$ cell trafficking, and with modest decreases in CD8+, DX5+ NK, and RB6-8C5+ PMN cells in the BAL cell population on day 5 p.i. By day 7 p.i., immunization decreases the numbers of all cell subsets examined.

EXAMPLE 12

Boosting with RSV B G-Protein Fragments Protects Against F1-A2 Induced Toxicity

Mice are immunized as in Example 9 and boosted with KLH conjugated peptide SEQ ID NO: 6 either at one day following immunization or four weeks following immunization. Similar results to those of both the A2 and CH17 peptides are observed with SEQ ID NO: 6. Mice boosted either at day 1 or four weeks following immunization with F1-A2 show reduced total cell counts in lavage fluid at 3, 5, and 7 days post RSV challenge. Correspondingly, eosinophilia is reduced at all three analyses days. IL-4 levels trend toward reduced levels. Finally, boosting mice with SEQ ID NO: 6 at either day 1 or four weeks produces no post-challenge weight loss in the same time period.

EXAMPLE 13

RSV Levels are Reduced by Antibodies Produced Following Immunization

Serum from individual mice is collected 14 days after the second of two subcutaneous administrations of an immunogen in alum, as described in Example 3. Aliquots of pre-titered RSV are mixed with serially diluted samples of individual mouse sera and incubated for 1 hr at room temperature and assayed for RSV neutralizing antibodies by plaque reduction assay. Mixtures are applied in duplicate to 24-well plates containing 60-80% confluent monolayers of Vero cells, adsorbed for 90 minutes at 4° C., followed by washing and incubation of the plates for 40 h at 37° C. in 1 ml of DMEM medium supplemented with 1% fetal calf serum. After incubation, the monolayers are fixed with acetone-methonal mixture and plaques enumerated by immunostaining with monoclonal anti-RSV antibodies. Plaque reduction is calculated as the plaque reduction neutralization titer$_{50}$ ($PRNT_{50}$), which is the reciprocal dilution of sera required to neutralize 50% of RSV plaques on a sub-confluent monolayer of Vero cells.

Immunization with peptide SEQ ID NOs: 4-6 or the multi-component vaccine incorporating the 163-190 RSV G A region polypeptide along with the 155-206 RSV G B region polypeptide demonstrate strong neutralizing antibody responses.

Patents and publications mentioned in the specification are indicative of the levels of those skilled in the art to which the invention pertains. These patents and publications are incorporated herein by reference to the same extent as if each individual application or publication was specifically and individually expressed explicitly in detail herein.

The foregoing description is illustrative of particular embodiments of the invention, but is not meant to be a limitation upon the practice thereof. The following claims, including all equivalents thereof, are intended to define the scope of the invention.

The invention claimed is:

1. A respiratory syncytial virus vaccine comprising an isolated immunogen that elicits a protective immune response that protects against an RSV vaccine enhanced RSV immune response said immunogen consisting of an amino acid sequence, said amino acid sequence consisting of the amino acids of:
   (i) amino acid position 163 to amino acid position 190 of SEQ ID NO: 8, amino acid position 163 to amino acid position 190 of SEQ ID NO: 7, or amino acid position 163 to amino acid position 190 of SEQ ID NO: 1;
   (ii) amino acid position 155 to amino acid position 206 of SEQ ID NO: 7, amino acid position 155 to amino acid position 206 of SEQ ID NO: 1, or amino acid position 155 to amino acid position 206 of SEQ ID NO: 8; or
   a combination thereof.

2. The vaccine of claim 1 wherein said immunogen further comprises a tag suitable for isolation of the immunogen.

3. The vaccine of claim 1 wherein said vaccine consists of the polypeptide of SEQ ID NO: 4 or 5.

4. The vaccine of claim 3 further comprising a second immunogen consisting of a polypeptide of SEQ ID NO: 3 or 6.

5. The vaccine of claim 1 wherein said immunogen consists of a polypeptide of SEQ ID NO: 4 or SEQ ID NO: 6.

6. A respiratory syncytial virus vaccine comprising an isolated immunogen that protects from an aberrant or enhanced response to an RSV vaccine in a human subject, said immunogen consisting of an amino acid sequence consisting of the amino acids of:
   (i) amino acid position 163 to amino acid position 190 of SEQ ID NO: 8, amino acid position 163 to amino acid position 190 of SEQ ID NO: 7, or amino acid position 163 to amino acid position 190 of SEQ ID NO: 1;
   (ii) amino acid position 155 to amino acid position 206 of SEQ ID NO: 7, amino acid position 155 to amino acid position 206 of SEQ ID NO: 1, or amino acid position 155 to amino acid position 206 of SEQ ID NO: 8; or
   a combination thereof; and
   an immunogenic carrier that promotes the immunogenicity of said immunogen, said immunogenic carrier coupled to said immunogen.

7. The vaccine of claim 6 wherein said immunogen is fused to a tag suitable for isolation of the immunogen.

8. The vaccine of claim 6 wherein said vaccine comprises an immunogen consisting of the polypeptide of SEQ ID NO: 4 or 5.

9. The vaccine of claim 8 further comprising a second immunogen consisting of a polypeptide of SEQ ID NO: 3 or 6 alone or coupled to an immunogenic carrier.

10. The vaccine of claim 6 wherein said vaccine comprises an immunogen consisting of the polypeptide of SEQ ID NO: 4 or SEQ ID NO: 6.

* * * * *

SEQUENCE LISTING

```
<160> NUMBER OF SEQ ID NOS: 8

<210> SEQ ID NO 1
<211> LENGTH: 298
<212> TYPE: PRT
<213> ORGANISM: respiratory syncytial virus

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
290                 295
```

<210> SEQ ID NO 2
<211> LENGTH: 13
<212> TYPE: PRT
<213> ORGANISM: respiratory syncytial virus

<400> SEQUENCE: 2

His Phe Glu Val Phe Asn Phe Val Pro Cys Ser Ile Cys
1               5                   10

<210> SEQ ID NO 3
<211> LENGTH: 52
<212> TYPE: PRT
<213> ORGANISM: respiratory syncytial virus

<400> SEQUENCE: 3

Pro Pro Ser Lys Pro Asn Asn Asp Phe His Phe Glu Val Phe Asn Phe
1               5                   10                  15

Val Pro Cys Ser Ile Cys Ser Asn Asn Pro Thr Cys Trp Ala Ile Cys
            20                  25                  30

Lys Arg Ile Pro Asn Lys Lys Pro Gly Lys Lys Thr Thr Thr Lys Pro
        35                  40                  45

Thr Lys Lys Pro
    50

<210> SEQ ID NO 4
<211> LENGTH: 28
<212> TYPE: PRT
<213> ORGANISM: respiratory syncytial virus

<400> SEQUENCE: 4

Phe His Phe Glu Val Phe Asn Phe Val Pro Cys Ser Ile Cys Ser Asn
1               5                   10                  15

Asn Pro Thr Cys Trp Ala Ile Cys Lys Arg Ile Pro
            20                  25

<210> SEQ ID NO 5
<211> LENGTH: 28
<212> TYPE: PRT
<213> ORGANISM: respiratory syncytial virus

<400> SEQUENCE: 5

Phe His Phe Glu Val Phe Asn Phe Val Pro Cys Ser Ile Cys Ser Asn
1               5                   10                  15

Asn Pro Thr Cys Trp Asp Ile Cys Lys Arg Ile Pro
            20                  25

<210> SEQ ID NO 6
<211> LENGTH: 52
<212> TYPE: PRT
<213> ORGANISM: respiratory syncytial virus

<400> SEQUENCE: 6

Pro Pro Lys Lys Pro Lys Asp Asp Tyr His Phe Glu Val Phe Asn Phe
1               5                   10                  15

Val Pro Cys Ser Ile Cys Gly Asn Asn Gln Leu Cys Lys Ser Ile Cys
            20                  25                  30

Lys Thr Ile Pro Ser Asn Lys Pro Lys Lys Pro Thr Ile Lys Pro
        35                  40                  45

Thr Asn Lys Pro
    50

<210> SEQ ID NO 7
<211> LENGTH: 292
<212> TYPE: PRT
<213> ORGANISM: respiratory syncytial virus

<400> SEQUENCE: 7

Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
                20                  25                  30

Leu Asn Leu Lys Ser Ile Ala Gln Ile Ala Leu Ser Val Leu Ala Met
            35                  40                  45

Ile Ile Ser Thr Ser Leu Ile Ile Ala Ala Ile Ile Phe Ile Ile Ser
        50                  55                  60

Ala Asn His Lys Val Thr Leu Thr Thr Val Thr Val Gln Thr Ile Lys
65                  70                  75                  80

Asn His Thr Glu Lys Asn Ile Ser Thr Tyr Leu Thr Gln Val Pro Pro
                85                  90                  95

Glu Arg Val Asn Ser Ser Lys Gln Pro Thr Thr Thr Ser Pro Ile His
                100                 105                 110

Thr Asn Ser Ala Thr Ile Ser Pro Asn Thr Lys Ser Glu Thr His His
            115                 120                 125

Thr Thr Ala Gln Thr Lys Gly Arg Ile Thr Thr Ser Thr Gln Thr Asn
130                 135                 140

Lys Pro Ser Thr Lys Ser Arg Ser Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Met Pro Lys
210                 215                 220

Lys Glu Ile Ile Thr Asn Pro Ala Lys Lys Pro Thr Leu Lys Thr Thr
225                 230                 235                 240

Glu Arg Asp Thr Ser Ile Ser Gln Ser Thr Val Leu Asp Thr Ile Thr
                245                 250                 255

Pro Lys Tyr Thr Ile Gln Gln Gln Ser Leu His Ser Thr Thr Ser Glu
            260                 265                 270

Asn Thr Pro Ser Ser Thr Gln Ile Pro Thr Ala Ser Glu Pro Ser Thr
        275                 280                 285

Leu Asn Pro Asn
    290

<210> SEQ ID NO 8
<211> LENGTH: 298
<212> TYPE: PRT
<213> ORGANISM: respiratory syncytial virus

<400> SEQUENCE: 8

Met Ser Lys Thr Lys Asp Gln Arg Thr Ala Lys Thr Leu Glu Lys Thr
1               5                   10                  15

Trp Asp Thr Leu Asn His Leu Leu Phe Ile Ser Ser Cys Leu Tyr Lys
                20                  25                  30

Leu Asn Leu Lys Ser Ile Ala Gln Ile Thr Leu Ser Ile Leu Ala Met

```
            35                  40                  45
Ile Ile Ser Thr Ser Leu Ile Ile Val Ala Ile Ile Phe Ile Ala Ser
    50                  55                  60

Ala Asn Asn Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Phe Phe Asn Leu Ser Gly Asn Thr Ser Gln Thr Thr
            100                 105                 110

Ala Ile Leu Ala Leu Thr Thr Pro Ser Val Glu Ser Ile Leu Gln Ser
        115                 120                 125

Thr Thr Val Lys Thr Arg Asn Thr Thr Thr Thr Gln Ile Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Asp Ile Cys Lys Arg Ile Pro Ser Lys
            180                 185                 190

Lys Pro Gly Lys Lys Thr Thr Thr Lys Pro Thr Lys Lys Pro Thr Ile
        195                 200                 205

Lys Thr Thr Lys Lys Asp Leu Lys Pro Gln Thr Thr Lys Pro Lys Glu
    210                 215                 220

Ala Pro Thr Thr Lys Pro Thr Glu Lys Pro Thr Ile Asn Ile Thr Lys
225                 230                 235                 240

Pro Asn Ile Arg Thr Thr Leu Leu Thr Asn Ser Thr Thr Gly Asn Leu
                245                 250                 255

Glu His Thr Ser Gln Glu Glu Thr Leu His Ser Thr Ser Ser Glu Gly
            260                 265                 270

Asn Thr Ser Pro Ser Gln Val Tyr Thr Thr Ser Glu Tyr Leu Ser Gln
        275                 280                 285

Pro Pro Ser Pro Ser Asn Ile Thr Asn Gln
290                 295
```